United States Patent [19]

Nashner et al.

[11] Patent Number: 5,303,715

[45] Date of Patent: Apr. 19, 1994

[54] APPARATUS AND METHOD FOR DETERMINING THE PRESENCE OF VESTIBULAR PATHOLOGY

[75] Inventors: Lewis M. Nashner; F. Owen Black; David J. Lilly, all of Portland, Oreg.

[73] Assignee: NeuroCom International, Inc., Clackamas, Oreg.

[21] Appl. No.: 951,042

[22] Filed: Sep. 23, 1992

Related U.S. Application Data

[63] Continuation of Ser. No. 426,463, Oct. 20, 1989, abandoned, which is a continuation of Ser. No. 600, Jan. 6, 1987, abandoned, which is a continuation-in-part of Ser. No. 895,783, Aug. 12, 1986, Pat. No. 4,830,024, which is a continuation-in-part of Ser. No. 873,125, Jun. 11, 1986, Pat. No. 4,738,269, which is a continuation of Ser. No. 408,184, Aug. 16, 1982, abandoned.

[51] Int. Cl.$^5$ .............................................. A61B 5/10
[52] U.S. Cl. ..................................... 128/782; 128/746
[58] Field of Search ............... 128/741, 742, 746, 747, 128/774, 782

[56] References Cited

U.S. PATENT DOCUMENTS

| | | | |
|---|---|---|---|
| 4,106,496 | 8/1978 | Proctor | 128/747 |
| 4,143,649 | 3/1979 | Foti | 128/746 |
| 4,325,386 | 4/1982 | Katz | 128/746 |
| 4,738,269 | 4/1988 | Nashner | 128/782 |

OTHER PUBLICATIONS

Nashner et al, Brain Research, 67, 1974, pp. 255–268.
Nashner et al, Ex. Brain Research, 36, 1979, pp. 463–476.
Cordo et al, J. Neurophysiology, vol. 47, No. 2, Feb. 1982, pp. 287–302.
Nashner et al, Brain Research, 150, 1978, pp. 403–407.
Nashner, Sensory Feedback in Human Posture Control, MIT, MVT–7003, Jun. 1970.
Kates et al, J. Med. Engr., vol. 4, No. 6, Nov. 1980.
Nashner, Exp. Brain Res., 30, 1977, pp. 13–24.
Nashner, "Analysis of Stance Posture in Humans," chapter 10 of Handbook of Behavioral Neurobiology, vol. 5.
Plenum Publishing, N.Y., N.Y., 1981, pp. 527–565.

*Primary Examiner*—Ruth S. Smith
*Attorney, Agent, or Firm*—Bromberg & Sunstein

[57] ABSTRACT

The presence of vestibular pathology is tested in an embodiment wherein the subject is placed on a support surface that is sway-referenced about an axis co-linear with the subject's ankle joints, if the subject is standing, or the subject's hip joints, if the subject is sitting. After the subject has assumed a position of equilibrium, a controlled external stimulus, such as an electrical, a caloric or a barometric stimulus, is applied to one or both of the subject's inner ears. It is then determined whether the stimulus produces a significant subject sway-response. In an alternative embodiment, the sway-response is monitored with the subject placed on a support surface that is sway-referenced about an axis perpendicular to the axis that is co-linear with the subject's ankle or hip joints. In another embodiment, the subject's visual orientation information is disrupted by means of a sway-referenced visual enclosure. In a further embodiment, the subject's head is aligned such that the sensitive axis of one vestibular end organ is aligned with the sway-reference axis.

31 Claims, 12 Drawing Sheets

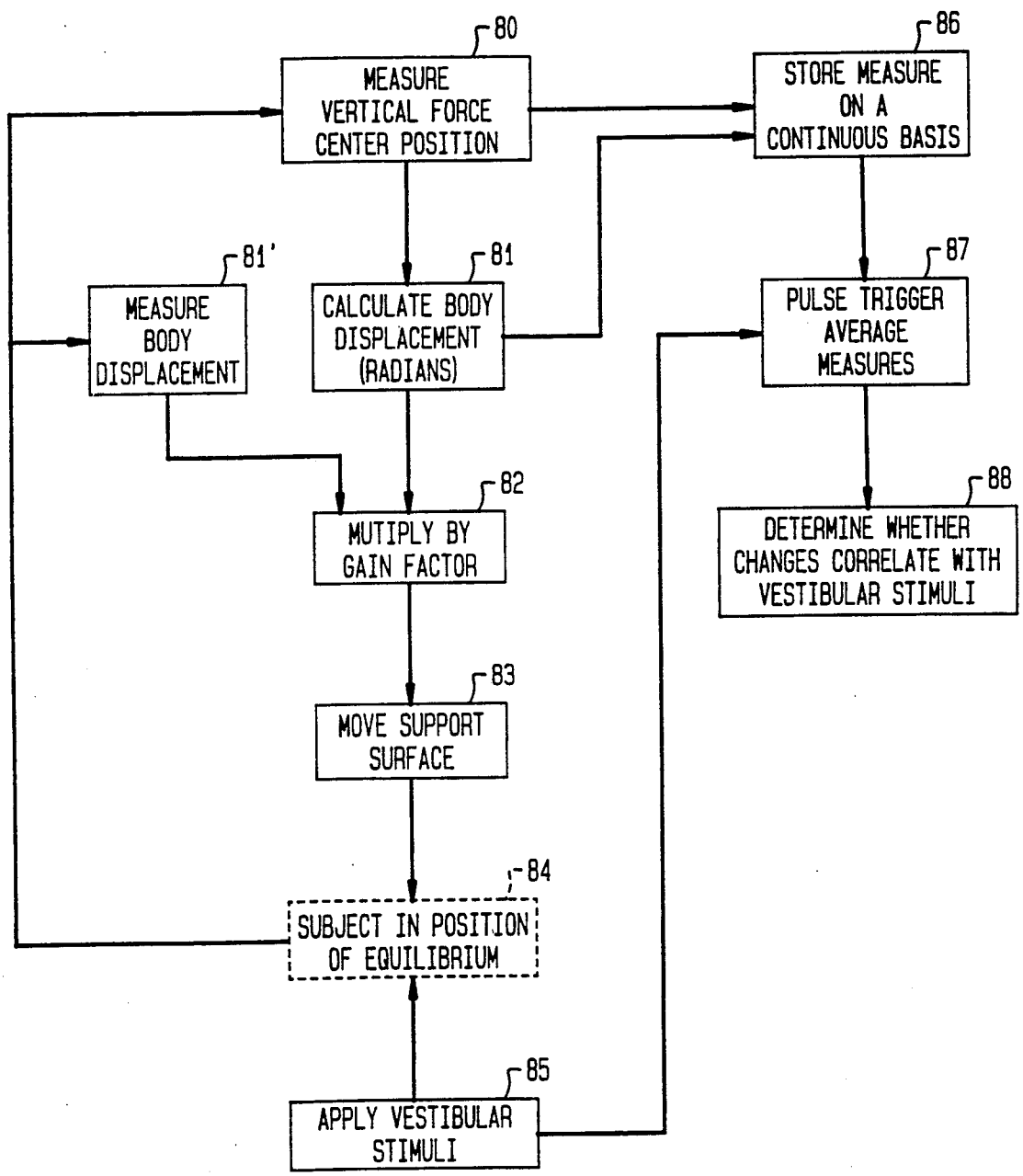

FIG. 9A
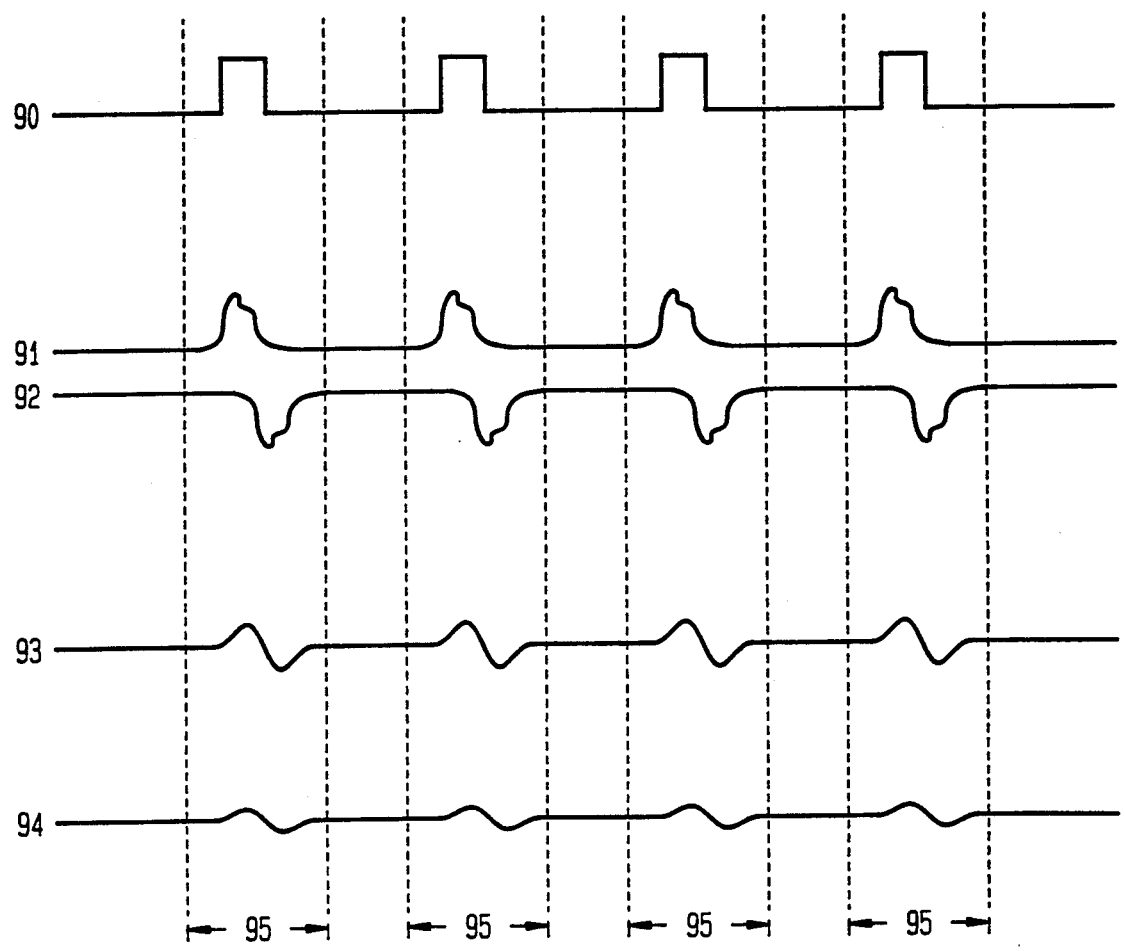
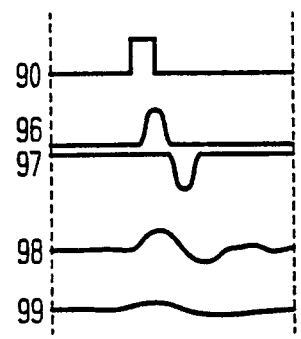

FIG. 9B
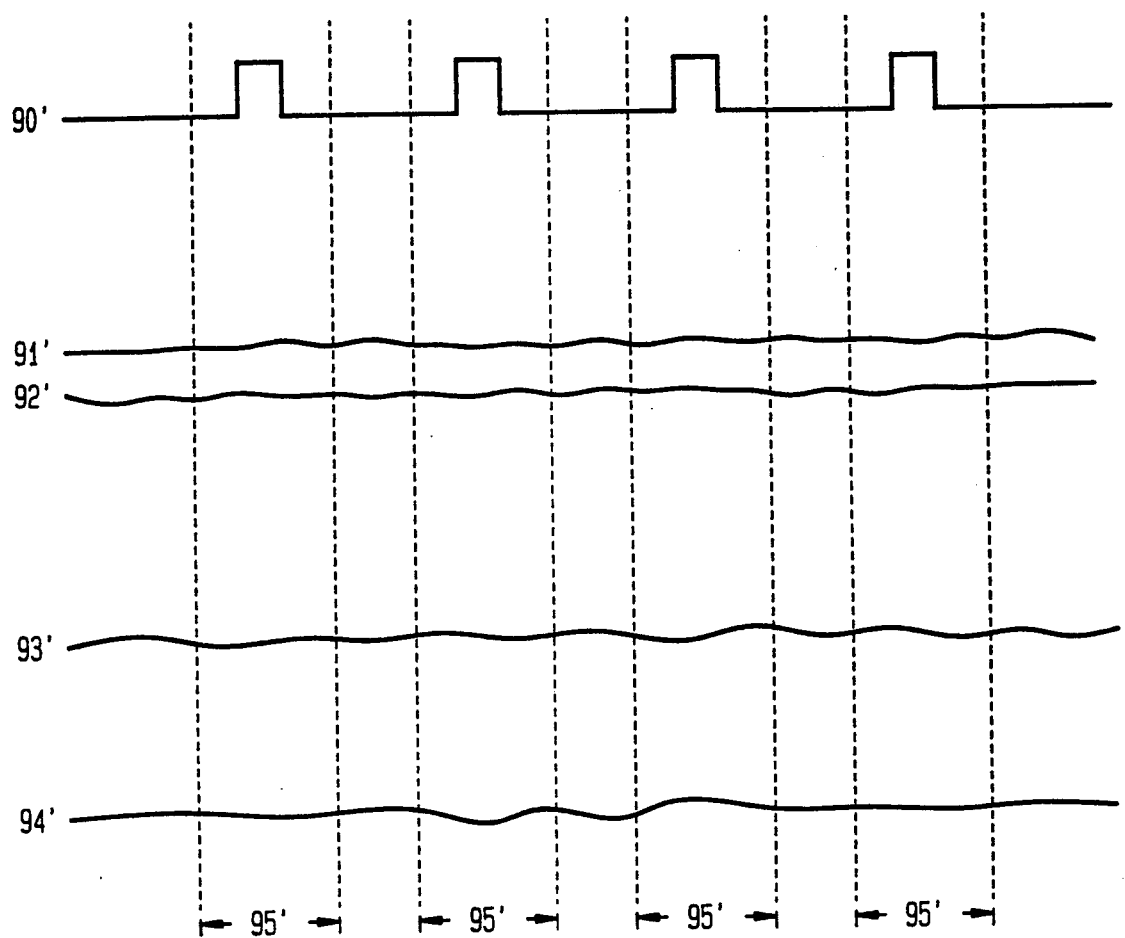
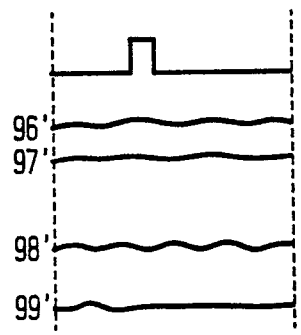

FIG. 9C
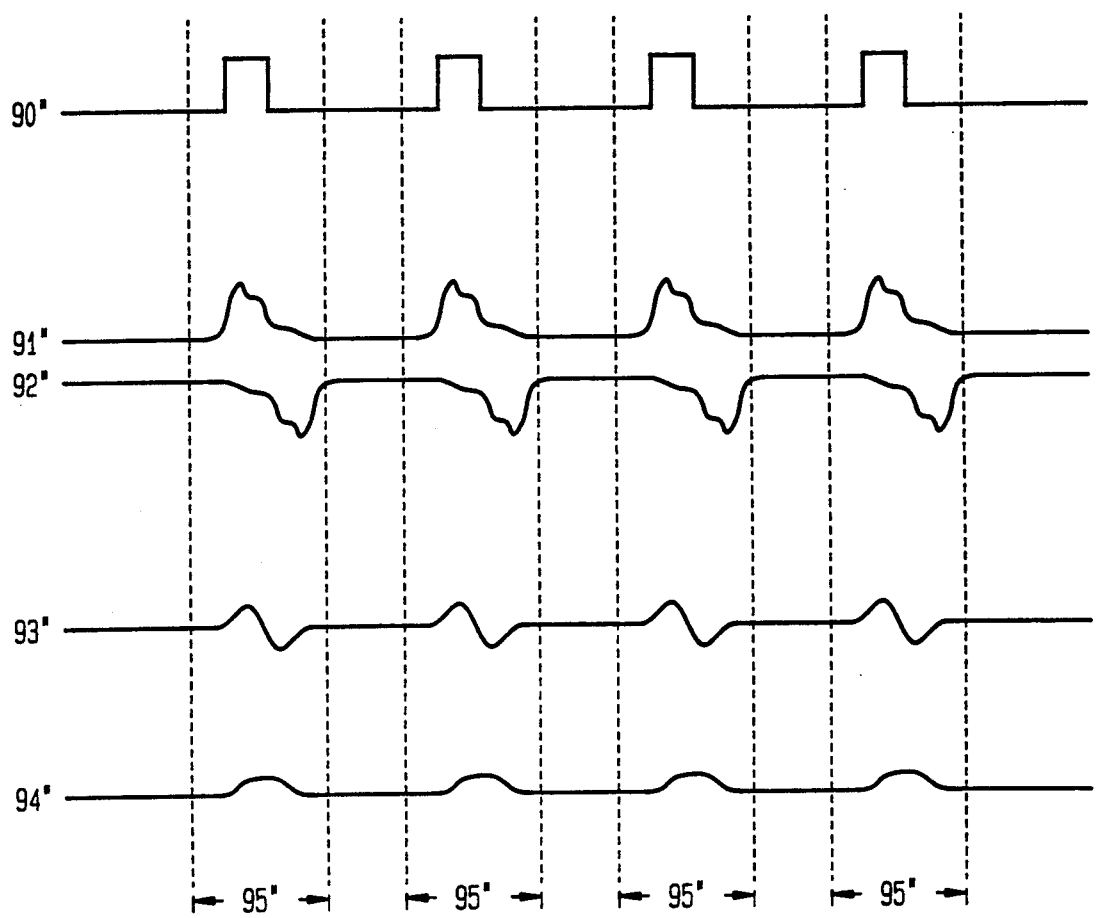
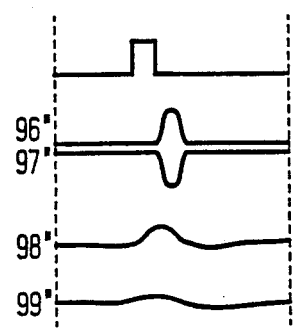

APPARATUS AND METHOD FOR DETERMINING THE PRESENCE OF VESTIBULAR PATHOLOGY

This application is a continuation of Ser. No. 426,463, filed Oct. 20, 1989, now abandoned, which in turn is a continuation of Ser. No. 000,600, filed Jan. 6, 1987, now abandoned, which in turn is a continuation-in-part of Ser. No. 895,783, filed Aug. 12, 1986, issued as Pat. No. 4,830,024 (after a file wrapper continuation), for an invention of Lewis M. Nashner et al., which is a continuation-in-part of Ser. No. 873,125, filed Jun. 11, 1986, issued as Pat. No. 4,738,269 (hereinbelow the "Nashner '269 Patent") for an invention of Lewis M. Nasher, which in turn is a continuation of Ser. No. 408,184, filed Aug. 16, 1982, for an invention of Lewis M. Nashner, now abandoned.

TECHNICAL FIELD

This invention relates generally to methods and devices for providing non-invasive, sensitive, and reliable tests for the presence of abnormalities in inner ear vestibular function. Such methods and devices are to be used as diagnostic tools for patients with symptoms of dysequilibrium, vertigo, and/or motion sickness.

BACKGROUND ART

The inner ear vestibular system is composed of two laterally symmetric sets of end organs (see for example Chapters 3 and 4 in Wilson, V. J., Melvill Jones, G., Mammalian Vestibular Physiology, Plenum Press, New York, 365 pp (1979). Each ear contains fine spatially specific end organs for sensing head accelerations. In each ear three semicircular canals sense angular, accelerations in three approximately orthogonal axes. The utricular otoliths sense the sum of gravity and linear head accelerations in a plane inclined approximately 30 degrees from horizontal. Function of the saccule is less understood but is believed to include gravity and linear acceleration along an approximately vertical axis. Thus, individual vestibular end organs are involved in maintaining different components of posture and equilibrium. The horizontal canals are used primarily to control horizontal plane eye and head movements, while the vertical canals and otoliths help maintain front-to-back and side-to-side balance of the head and trunk. The spatial and functional specificity within the vestibular system provides an opportunity for selectively determining the extent of pathology of individual end organs by observing both head, eye, and body responses to vestibular stimulation.

It is also known that the canal and otolith end organs sense different frequency components of linear and angular motion. Canals sense angular acceleration frequencies over the range of 0.1 to approximately 5 Hz, while the otoliths sense lower frequency linear accelerations in the range of 0 to 0.1 Hz (Meary, J. L., the vestibular system and human dynamic space orientation, NASA CR-628 (1966)). Thus, the use of frequency selective signals is another possible means for isolating the function, of individual vestibular end organs.

Vestibular pathology frequently affects only a portion of the vestibular end organs, sometimes in one ear and other times distributed either equally or unequally among the organs of the two ears (see, for example, Schuknecht, H. F., Pathology of the ear, Harvard University Press, Cambridge, Mass. (1974)). While, the treatment of choice for the patient with vestibular pathology depends on the distribution and extent of involvement among the ten end organs, the symptoms of the individual patient frequently do not reveal which organs are affected. Hence, objective methods for assessing the function of individual vestibular end organs are essential to the comprehensive vestibular examination.

To test vestibular functions head acceleration, stimuli can be imposed with precise time course, amplitude, and spatial specificity. However, precise acceleration stimuli cannot be effectively used to test vestibular end organs individually, because the lateral symmetry of the two inner ears means that acceleration in any one axis will always excite end organs in both ears. Hence, several alternative means for selective stimulation of end organs in a single ear have been developed using non-physiologic inputs: (1) Using so called "galvanic" vestibular stimulation, end organs of one ear can be electrically excited by passing small currents between two or more surface electrodes affixed to the mastoid bone of the ear or other locations on the head (see, for example, Nashner, L. M., Wolfson, P., Influence of head position and proprioceptive cues on short latency postural reflexes evoked by galvanic stimulation of the human labyrinth, Brain Research 67: 255-268 (1974)). (2) The so called "caloric" stimulus excites the horizontal semicircular canal end organ of one ear by creating a thermally induced pressure gradient within the horizontal canal (see, for example, Dayal, V. S., Farkashidy, J., Kuzin, B., Clinical evaluation of the hot caloric test as a screening procedure, Laryngoscope 83: 1433 (1973)). (3) In some instances changes in air pressure between the external canal and middle ear spaces of one ear can excite one or more end organs in that ear (see for example Daspit, C. P. Churchill, D., Linthicum, F. H., Diagnosis of perilymph fistula using ENG and impedance, Laryngoscope 90: 217-223 (1980).

Various attempts have been made to use the "galvanic" vestibular stimulus as a clinical diagnostic tool (for examples, Ishihara, A., Galvanic stimulation of the labyrinth, Jap. J. Otol. Tokyo 24: 482 (1918); Fischer, J. J., Galvanic reaction, The labyrinth, Grune and Stratton Inc, New York (1956); Pfaltz, C. R., Koike, Y., Galvanic test in central vestibular lesion, Acta, Otolarying. (Stockh) 65: 161 (1968)). In this test the vestibular end organs are selectively stimulated by passing small electrical currents between electrodes placed in different configurations on the mastoid bones. Placing one electrode on each mastoid bone stimulates receptors in both inner ears in opposite directions, while two electrodes placed on a single mastoid bone stimulate receptors of one ear selectively. While the time course, amplitude, and frequency of electrical current stimuli can be precisely controlled, the distribution of stimulation among the 5 end organs of the stimulated ear can be accomplished only to a limited degree by altering the placement of the electrodes. Responses to electrical vestibular stimulation can be monitored as movements of the eyes (for example, Hozawa, J., A clinical consideration on the nature of electrically stimulated nystagmus, Otologica, Tokyo 33: 939 (1961)) or in the standing subject as body swaying (for example, Coats, A. C., Stolz, M. S., the recorded body sway response to galvanic stimulation of the labyrinth, Laryngoscope 79: 85 (1969); Coats, A. C., Effects of varying stimulus parameters on the galvanic body sway response, Ann. Otol. 82: 96 (1973)).

Electrical stimulation of the vestibular receptor organs is a potentially useful clinical diagnostic method, because it can be used to quantify receptor function of one ear at a time and because the time course and frequency of stimulation can be precisely controlled. Electrical vestibular testing for this or any other purpose, however, is not currently a standard of practice in the clinic. This is because relatively large currents are required to produce postural or eye movement responses when the subject is tested under passive seated or reclining positions. Large stimulus levels can cause the patient significant discomfort. Furthermore, the resulting eye movement and sway responses are small, making the repeatability and reliability of the resulting measurements poor.

The use of "caloric" stimulation is already a standard practice in the currently used clinical vestibular examination, and several manufacturers produce caloric stimulation devices for this purpose. With the caloric test, the patient assumes a passive reclining position on a chair or bed. The head is positioned tilted 30 degrees back so that the plane of the horizontal canals is oriented roughly vertical. Then, hot or cold water is introduced to one ear and the amplitude and duration of nystagmoid eye movement responses are observed subjectively or measured using electronystagmography (ENG's). Alternatively, bilateral stimuli can be imposed by introducing thermal stimuli of either the same or opposite temperatures to the two ears simultaneously.

The caloric test is currently used by clinicians to identify asymmetries in function between the two ears. The sensitivity and specificity of this method is limited, however, for several reasons. First, with currently available methods, the thermal input stimulates only the horizontal canals and therefore does not detect asymmetries involving the vertical canals or otoliths. Second, the amplitude and frequency of the thermal stimulus cannot be controlled precisely, because heat conduction through the temporal bone is slow and varies among patients. Thus, the time course of the thermal vestibular stimulus is also slow and tests only the lowest frequency component of the horizontal canal response. Third, patients frequently become dizzy, motion sick, or nauseous with the caloric test.

The third method for selectively stimulating one or more vestibular end organs is to alter the pressure between the external and middle ear spaces. As with the caloric vestibular test, pressure stimuli are introduced with the patient in a passive seated or standing position.

DISCLOSURE OF INVENTION

The present invention provides new methods and apparatus for significantly improving the specificity, accuracy, and reliability of non-invasive tests for the presence of inner-ear vestibular disorders. The present invention does not propose novel ways for selectively stimulating inner ear vestibular end organs. Rather, it provides new methods and devices for placing the subject in tasks where an equilibrium position is actively controlled, stimulating the vestibular end organs, and then measuring the subject's displacements from the maintained equilibrium position in response to the stimulation.

In accordance with methods of the present invention, the subject performs an active posture control task by assuming a position in equilibrium on a movable support surface and within a second independently movable visual enclosure. First, one or more quantities related to displacements of the subject's body from the assumed equilibrium position are measured. Second, either one or both of the support surface and visual enclosure are moved in functional relation to one of the measured quantities. Moving the support surface and visual enclosure in functional relation to the subject's displacements from equilibrium disrupts information about the subject's equilibrium position normally available from the visual and somatosensory inputs. Under these altered sensory conditions, the subject must actively maintain equilibrium by increasing his reliance on vestibular orientation information.

The conditions in which the support surface and visual enclosure are moved in functional relation to a quantity related to the subject's displacements from equilibrium are referred to herein as "sway-referenced" support and visual conditions, respectively. The term "sway-referenced" is used, because the surfaces used as orientation references by the somatosensory and visual systems move in relation to the subject's displacement from the assumed equilibrium position rather than remain fixed in relation to gravity. If the subject relies on somatosensory or visual inputs during sway-referenced conditions, then he will have an inaccurate perception of his position in equilibrium.

The the axis about which the support surface and visual enclosure move during sway-referencing the "sway-reference is herein referred to as axis". Information about the subject's position in equilibrium is disrupted only in the axis of body motion aligned with the sway-reference axis.

The extent to which sway-referencing disrupts somatosensory and visual information about the subject's position in equilibrium in the sway-reference axis can be modified. During sway-referenced conditions, the amplitude of the support surface and visual enclosure motions can be equal to, a fraction of, or a multiple of the measured quantity related to the subject's displacement from equilibrium. When the support surface and visual enclosure movements are equal to the measured quantity, then orientation information in the direction of displacement aligned to the sway-reference axis is substantially disrupted. When support and enclosure movements are a fraction of the measured quantity of the subject's displacement from equilibrium, the perception of displacement from a position in equilibrium will be reduced. The term "sway-reference gain" means the amplitude relation between the measured quantity of body displacement from equilibrium and the motion of the sway-referenced surface.

Depending on the overall medical status of the subject, the inner ear vestibular system can be stimulated while the subject assumes an active posture control task in various different positions in equilibrium. In one preferred embodiment, the subject assumes an erect standing position in equilibrium. According to methods already described in the Nasher '269 Patent, the support surface and visual enclosure are each sway-referenced to a measured quantity related to the antero-posterior displacements in the subject's center of body mass by rotating these surfaces about a common axis of rotation approximately co-linear with the ankle joint axis. In this embodiment, the sway-reference axis is aligned with the antero-posterior axis of the subject's body sway. As described in further detail below, numerous other embodiments are possible.

BRIEF DESCRIPTION OF THE DRAWINGS

FIG. 8 shows a block diagram of the principal steps of a possible embodiment of a method according to the present invention.

FIGS. 9A, 9B and 9C illustrate the sequence of events measured during an electrical test of the left superior and right inferior semicircular canal end organs conducted according to a preferred embodiment of a method shown in FIG. 8.

DESCRIPTION OF SPECIFIC EMBODIMENTS

Figure 1:
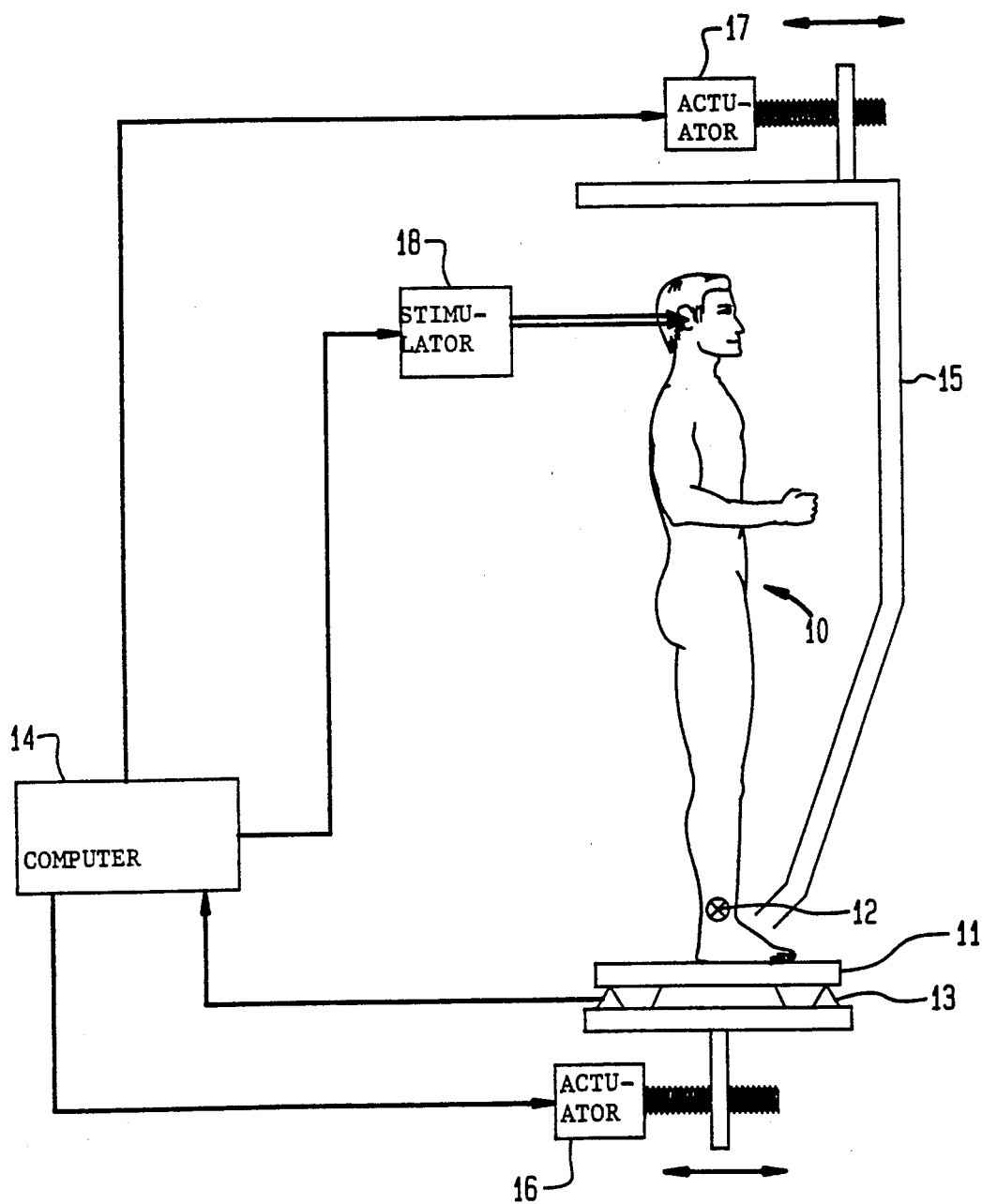
FIG. 1 shows a schematic block diagram of the principal components of a possible embodiment of an apparatus according to the present invention.

In the Nasher '269 Patent, a method and apparatus were described which force a subject to use vestibular orientation information while maintaining a position in equilibrium. Somatosensory (inputs from contact with the support surface) and visual orientation inputs to the subject are made inaccurate and thereby disrupted for sensing position in equilibrium by: (1) placing the subject on a movable support surface and within a separately movable enclosure completely surrounding his field of view, (2) measuring one or more quantities related to the spontaneously occurring displacements of the subject away from the equilibrium position, and then (3) moving either one or both of the support surface and visual enclosure in functional relation to one of the measured quantities.

In two preferred embodiments of the invention of the Nashner '269 Patent, the two reference structures (the support surface and the visual enclosure) are each independently rotatable about the sway-reference axis. In one preferred embodiment, the subject stands erect with his ankle joints either co-linear with or perpendicular to the rotational axes of support surface and visual enclosure. In another preferred embodiment, the subject is seated on the support surface with the rotational axis of the hip joints either co-linear with or perpendicular to the rotational axes of the support surface and visual enclosure.

According to a preferred protocol of the invention of the Nasher '269 Patent, the support surface, the visual enclosure, or both, rotate in direct functional relation to the rotational displacements of the subject's center of body mass in relation to the feet. These are called "sway-referenced" support surface and visual conditions, respectively. Under sway-referenced support surface conditions with eyes closed or sway-referenced support and visual surface conditions with eyes open, a subject who may be seated or standing on the platform support surface is forced to rely on vestibular inputs to maintain his position in equilibrium. Under these conditions, therefore, the patient is maximally dependent on vestibular stimuli to maintain the assumed equilibrium position.

In addition to the embodiment where the sway-reference axis is aligned with the antero-posterior axis of the subject's body sway, in a second embodiment, the subject can stand with the support surface and visual enclosure axes perpendicular to the ankle joint axis, and the support surface and visual enclosure sway-referenced to the side-to-side displacements in the subject's center of body mass. In this embodiment, the sway-reference axis is aligned with the side to side direction of body sway.

In addition to the above described positions, the subject's head can be positioned to align the sensitive axis of one vestibular end organ of one ear with the sway-reference axis. When the subject is positioned with the ankle joints aligned to the sway-reference axis and the head turned 45 degrees to the left, for example, the sensitive axes of the inferior vertical canal end organ of the right ear and the superior vertical canal end organ of the left ear are each aligned with the sway-reference axis. With the head turned 45 degrees to the right, the sensitive axes of the superior vertical canal end organ of the right ear and the inferior vertical canal end organ of the left ear are now aligned with the sway-reference axis. With the subject positioned ankles perpendicular to the sway-reference axis and the head tilted back 60 degrees, the sensitive axes of the left and right ear horizontal canal end organs are aligned with the sway-reference axis of the support surface and visual enclosure.

If a stimulus is introduced to one ear with the sensitive axis of one vestibular end organ aligned with the sway-referenced axis, then the subject will be maximally dependent on orientation information from the end organ aligned to the sway-reference axis and therefore maximally sensitive to stimulation of the aligned vestibular end organ. Thus, by stimulating the vestibular system of one ear with the head and body repositioned in relation to the sway-reference axis, each inner ear vestibular end organ can be selectively tested for sensitivity to stimulation.

If the condition of the subject does not allow testing in an erect standing position, then the subject can maintain an erect seated position in equilibrium and be tested using procedures similar to those described above. In one embodiment of the erect seated position test, the axes of the support surface and visual enclosure are aligned co-linear with the hip joints. With this alignment, the support surface and visual enclosure are sway-referenced by rotating them in functional relation to the antero-posterior displacements of the subject's center of trunk mass from equilibrium. In this position, the sway-reference axis is aligned with the antero-posterior direction of trunk sway.

Alternatively, the hip joint axis can be aligned perpendicular to the rotational axis of the support surface and visual enclosure. With this alignment, the surfaces are rotated in relation to the side-to-side displacements of the subject's center of trunk mass from equilibrium. In this position, the sway-reference axis is aligned with the side-to-side direction of trunk sway.

In the seated embodiment of the test, the subject's head can also be turned to one side or tilted backward to selectively align a single vestibular end organ of one ear with the sway-reference axis.

It can be appreciated that the embodiments of the present invention involve placing the subject in an active equilibrium control task, positioning the subject's body and head in relation to the sway-reference axes of the support surface and visual enclosure, and then sway-referencing the support surface and visual enclosure to selectively sensitize a single vestibular end organ to stimulation, and embodiments are not limited to the erect standing or seated positions. For example, the rotational axis of the support surface and visual enclosure can be aligned with one of the three axes of head rotation at the neck joint. The support surface and visual enclosure can then be sway-referenced to the antero-posterior or side-to-side tilting of the head. And, the rotational axis of the visual enclosure can be aligned with an axis of eye rotation in the head and the enclosure sway-referenced to the rotational motions of the eyes.

The method described herein for sway-referencing the support surface and visual enclosure can also be performed about several axes at the same time. Multiple axis sway-referencing requires a support surface and visual enclosure capable of rotation about a plurality of axes.

It can also be appreciated that the responsiveness of individual vestibular end organs to stimulation can be tested selectively while the subject maintains a position in equilibrium with the support surface and visual enclosure sway-referenced one at a time. Furthermore, vestibular end organ responsiveness to stimulation can be selectively determined by using sway-reference gains less or greater than unity. Gains less than unity are required for subjects who cannot maintain positions in equilibrium with sway-reference gains of unity. Gains greater than unity may be required for the subject with exceptionally good balance control.

Depending on what aspect of inner-ear vestibular function is to be selectively tested under sway-referenced support surface and/or visual enclosure conditions, three different forms of controlled vestibular stimuli can be used:

(1) If the purpose of the test is to identify selective losses in vestibular function, vestibular end organs of one ear can be selectively stimulated using controlled electrical currents. Electrically stimulating the vestibular end organs of one ear while a subject maintains a position in equilibrium with the sway-reference axes of the support surface and visual enclosure aligned with the sensitive axis of a single end organ of the ear is a new clinical method for detecting vestibular abnormalities in the stimulated ear. By selectively increasing the responsiveness of the posture control system to stimulation of the aligned vestibular end organ, stimulus intensities are reduced (reducing pain and discomfort) and the sensitivity and reliability of measurements increased. Furthermore, by aligning the sway-reference axis with the sensitive axis of a single vestibular end organ, the responsiveness of each end organ can be tested selectively.

(2) A second means to stimulate the vestibular end organs of one ear while the subject maintains a position in equilibrium under sway-referenced conditions is to introduce controlled thermal stimuli to the external ear canal. In this new version of the caloric test, the sensitivity and reliability of the resulting measurements of vestibular function are improved by stimulating the vestibular system and measuring the subject's resulting displacements from equilibrium while the subject's posture control system is maximally sensitive to the vestibular stimulus. As with the electrical stimulus method, the sway-reference axis of the visual enclosure and support surface can be aligned with the sensitive axis of a given vestibular end organ to selectively test the responsiveness of individual end organs.

(3) The vestibular receptors can also be stimulated by introducing controlled changes in air pressure to the external canal of one ear. If the subject has one or more abnormal connections between the perilymph fluid and the inner ear space (perilymph fistula), then one or more vestibular end organs will be stimulated by the pressure change. In the Nasher '269 Patent, a method is described for increasing the sensitivity and reliability of measurements of the subject's abnormal responsiveness to ear pressure stimulation. The present invention provides additional new methods for identifying on a selective basis which vestibular end organ or organs are abnormally responsive to pressure stimulation by aligning the sensitive axis of a vestibular end organ with the sway-reference axes of the support surface and visual enclosure. Furthermore, the present invention provides methods for performing the pressure test with the subject in seated and other positions in equilibrium.

The equilibrium position of the body and displacements of the body from equilibrium can be measured by one or a combination of means, all well known in the prior art:

(1) The contractile activity of the muscles generating the internal body forces for maintaining the equilibrium position can be measured using electromyographic (EMG) recordings. If the subject is maintaining an erect standing position in equilibrium, then ankle joint EMGs such as gastrocnemius and tibialis anterior can be recorded. If the subject maintains an erect seated position, then lower trunk EMGs, such as paraspinals and abdominals, are recorded.

(2) The support surface reaction forces maintaining the subject's equilibrium position can be recorded using a forceplate. Forceplates suitable for this purpose are manufactured by several companies (Kistler Corporation, 75 John Glen Drive, Amherst, N.Y., 14120; Advanced Mechanical Technology, Inc., 141 California Street, Newton, Mass. 02158; and NeuroCom International, Inc., 9570 S.E. Lawnfield Road, Clackamas, Oreg. 97015. The antero-posterior and side-to-side positions of the center of vertical force are particularly useful forceplate measures, because they can be used to calculate the approximate antero-posterior and lateral angular orientation of the center of body mass in relation to the ankle joints.

(3) Several means are available to measure directly the position of the body. Displacement transducers can be attached directly to the body. Alternatively, body positions can be measured by several commercially available computerized optical systems (Northern Digital Ltd., 415 Phillip Street, Waterloo, Ontario, Canada N2L 3XQ).

In a preferred embodiment of the present invention, the subject is placed on a movable support surface, and the subject assumes an erect standing position in equilibrium. The subject's field of view is substantially surrounded with the visual enclosure, which is independently movable. The ankle joints are aligned with the sway-reference axis of the support surface and the visual enclosure. The subject's head is positioned 45 degrees to the left or right or tilted 60 degrees back to align the sensitive axis of one vestibular end organ with the sway-reference axis. The subject's displacements from equilibrium in the antero-posterior direction are measured on a continuous basis, and the support surface, the visual enclosure, or both are moved in functional relation to the measured displacements of the subject. Transient electrical, pressure, or thermal stimuli are introduced to one ear at a time. Then, the time course of the subject's displacements from the assumed equilibrium position in the absence of vestibular stimulation is compared to that during stimulation using statistical methods well known in the prior art. The extent of statistically significant changes in equilibrium position correlated with vestibular stimulation is a measure of the responsiveness of the aligned canal end organ to the imposed stimulation.

In a second preferred embodiment, the subject is placed on a movable support surface and assumes an erect seated position in equilibrium. The subject's field of view is substantially surrounded with the visual enclosure, which is also independently movable. The hip joints are aligned with the support surface and visual enclosure sway-reference axes. The subject's head is positioned 45 degrees to the left or right or tilted 60 degrees back to align the sensitive axis of one canal end organ with the sway-reference axis. Displacements of the subject's trunk from equilibrium in the antero-posterior direction are measured on a continuous basis, and the support surface, the visual enclosure, or both are moved in functional relation to the measured displacements of the subject. Transient electrical, pressure, or thermal stimuli are introduced to one ear-at a time. Then, the time course of the subject's displacements from the assumed equilibrium position in the absense of vestibular stimulation is compared to that during stimulation using statistical methods well known in the prior art. The extent of statistically significant changes in equilibrium position correlated with vestibular stimulation is a measure of the responsiveness of the aligned canal end organ to the imposed stimulation.

In a further specific embodiment based on the second preferred embodiment, the subject stands on a support surface, and the support surface and visual enclosure are each independently rotatable about a common axis co-linear with the subjects ankle joints. The support surface rests on three or more vertical force transducers. A digital computer samples signals from the force transducers and calculates the position of the center of vertical force exerted by the subject's feet onto the surface and the antero-posterior angular position of the subject's center of body mass in relation to the ankle joints. The computer controls on a continuous basis the rotational positions of the support surface and visual enclosure, such that one or both of these surfaces rotate in functional relation to the calculated position of the center of vertical pressure or angular orientation of the subject's center of body mass. The computer stores on a continuous basis the results of calculations of the center of vertical force position and the angular position of the center of body mass in relation to the ankle joints. The computer initiates and controls stimuli to the vestibular system of one ear. Depending on the statistical methods used to calculate the significance of body displacements correlated with the vestibular stimuli, brief pulses of stimulation or continuously varying vestibular stimuli can be used. The computer then performs additional calculations using methods well known in the prior art to determine the statistical significance and extent of displacements from the equilibrium position correlated with the transient vestibular stimuli.

The following three versions of vestibular stimulation are used to determine different aspects of vestibular function:

(1) Pressure stimuli are used to identify abnormal connections between the middle and inner ear space. Pressure stimuli are introduced by inserting a tympanometer probe into the external canal and coupling the other end of the tube to a pressure generating device. The pressure generating device is controlled on a continuous basis by the computer.

(2) Electrical stimuli can be introduced to the vestibular system in several different configurations. Placing one surface electrode on each of the two mastoid bones and passing a controlled current between the electrodes stimulates end organs in both ears. Placing two adjacent electrodes on a single mastoid bone selectively stimulates end organs of that ear. Electrical current between the two electrodes can be controlled on a continuous basis using a current generating device operating under the control of the computer.

(3) The vestibular end organs of one ear are thermally stimulated by introducing temperature controlled water or air to the external canal of the ear. The device for irrigating the ear with temperature controlled water or air can also be under the control of the computer.

It should be appreciated that other embodiments of the present invention can also be used to test the subject's postural reactions to controlled changes in air pressure, electrical current, or thermal stimuli while the subject is maximally sensitive to the resulting vestibular inputs. By placing the subject with eyes closed in a position in equilibrium on a movable support surface and then moving the support surface in functional relation to the displacements of the subject from the equilibrium position, the movable visual enclosure can be eliminated. Now, the subject's posture control system is maximally sensitive to vestibular inputs, because the subject is deprived of vision while somatosensory information derived from contact with the support surface is inaccurate.

In a further simplification of this embodiment, the subject maintains a position in equilibrium on a passively compliant, rather than an actively movable, support surface. For example, if the subject maintains a standing position in equilibrium on a support surface with a purely elastic compliance about a rotational axis co-linear with the ankle joints, then the rotational orientation of the support surface is substantially related to the antero-posterior displacements in the position of the center of vertical force exerted by the subject's feet on the support surface. If a combination of elastic and viscous compliant elements is used in this embodiment, then rotations of the support surface will lag in time behind those of the center of vertical force. The correct combination of elastic and viscous forces, however, will result in a support surface displacement which is substantially in relation to the angular displacements of the subject's center of body mass.

It should also be appreciated that the visual enclosure can also be moved in functional relation to the subject's displacements from the equilibrium position without an active controlling element. Specifically, a light-weight visual enclosure can be attached to a support surface compliant about a rotational axis co-linear with the ankle joints. In this embodiment, both the support surface and visual enclosure will rotate together.

FIG. 1 shows a schematic block diagram of the principal components of an embodiment of an apparatus according to the present invention. In this embodiment, the subject 10 stands erect in a position of equilibrium on a support surface 11, which is rotatable about an axis 12 co-linear with the ankle joints. The support surface rests on vertical force transducers 13, the signals from which are transmitted to the computer 14 for calculating angular displacements of the subject's center of body mass from the equilibrium position. The subject's field of view is substantially surrounded by an enclosure 15 which is also rotatable about an axis co-linear with the ankle joints 12. The computer 14 generates signals which, by way of position actuators, rotate the support surface 11 and visual enclosure 15 in functional relation to the computed angular displacement of the subject's center of body mass. Then, the computer, by way of an actuator for stimulating the inner ear vestibular system 18, initiates and controls a stimulus to one of the subject's ears and then computes whether or not the stimulus produces correlated and significant increases in one or more of the measured variables of postural activity.

Figure 2:
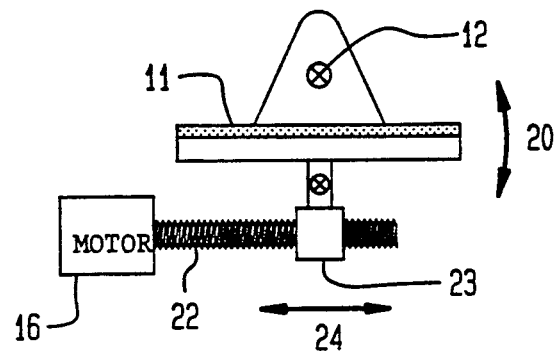
FIG. 2 Shows an apparatus for controlling the rotational position of a support surface in one embodiment of the invention.

FIG. 2 shows one means for controlling the rotational position 20 of the support surface 11 about a rotational axis 12 approximately the height of the ankle joints above the surface, using a system comprising an electric motor 21, a lead screw 22, and a ball nut 23. Rotations of the motor and lead screw move the ball nut back and forth 24 and thereby rotate the support surface 11. It can be appreciated that a similar system consisting of an electric motor, a lead screw, and a recirculating ball nut can be used to rotate the visual enclosure. Alternatively, the rotational positions of the support surface and visual enclosure can be controlled by a system consisting of an electric motor, a fixed displacement hydraulic pump, and a hydraulic cylinder.

Figure 3:
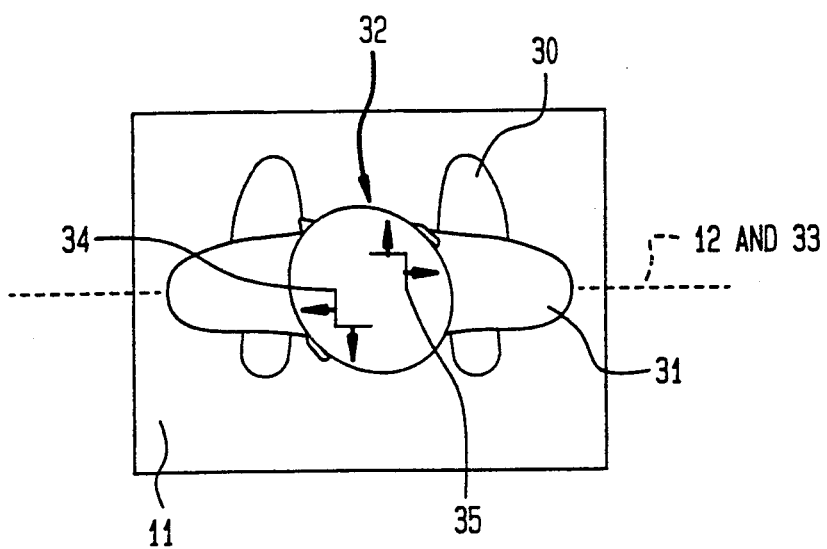
FIGS. 3-5 show various ways of positioning the subject's feet, body and head in one embodiment of the invention.

FIG. 3 shows a preferred embodiment for positioning the subject's feet 30, body 31, and head 32 to align the sway-reference axis with the sensitive axes of the left superior 34 and right inferior 35 semicircular canal end organs. In the standing embodiment of the test, the subject stands on the rotatable support surface 11 with the ankle joint axis 33 co-linear to the common support surface and visual enclosure rotation axis 12 and with the head 32 turned 45 degrees to the left. In the seated embodiment of the test (not shown), the subject sits on the rotatable support surface and within the rotatable visual enclosure with the hip joint axis co-linear to the common support surface and visual enclosure rotation axis and with the head turned 45 degrees to the left. To determine the responsiveness of the left superior vertical canal receptor end organ, controlled vestibular stimuli are introduced to the left ear. To determine the responsiveness of the right inferior canal end organ, the right ear is stimulated.

Figure 4:
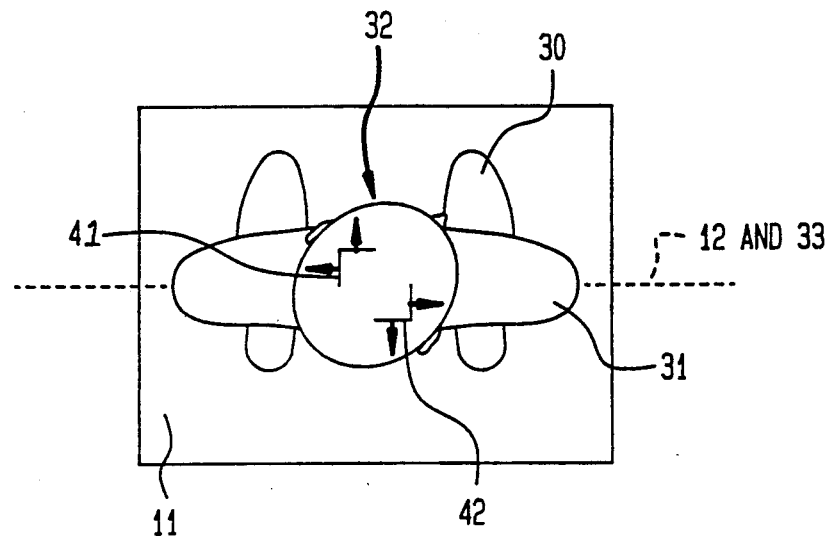

The sensitive axes of the left inferior 41 and right superior 42 semicircular canal end organs are aligned with the sway-reference axis as shown in FIG. 4. In the standing embodiment of the test, the subject stands on the rotatable support surface 11 and within the rotatable visual enclosure with the ankle joint axis 33 co-linear to the common support surface and visual enclosure rotation axis 1 and with the head 32 turned 45 degrees to the right. In the seated embodiment (not shown), the subject sits on the rotatable support surface and within the rotatable visual enclosure with the hip joint axis co-linear to the common support surface and visual enclosure rotation axis and with the head turned 45 degrees to the right. To determine the responsiveness of the left inferior vertical canal receptor end organ, controlled vestibular stimuli are introduced to the left ear. To determine the responsiveness of the right superior canal end organ, the right ear is stimulated.

Figure 5:
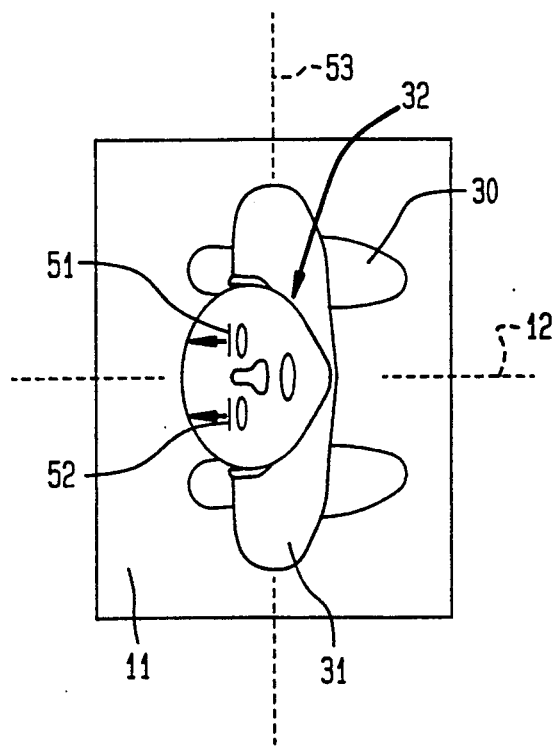

The sensitive axes of the left 51 and right 52 horizontal semicircular canal end organs are aligned with the sway-reference axis as shown in FIG. 5. In the standing embodiment of the test, the subject stands on the rotatable support surface 11 and within the rotatable visual enclosure with the ankle joint axis 53 perpendicular to the common support surface and visual enclosure rotation axis 12 and with the head 32 tilted back 60 degrees. The seated embodiment is substantially similar to the standing embodiment, but the subject is positioned on the rotatable support surface and within the rotatable visual enclosure with the hip joint axis perpendicular to the common support surface and visual enclosure rotation axis and with the head tilted back 60 degrees. To determine the responsiveness of the left horizontal canal receptor organ, controlled vestibular stimuli are introduced to the left ear. To determine the responsiveness of the right horizontal end organ, the right ear is stimulated.

Figure 6:
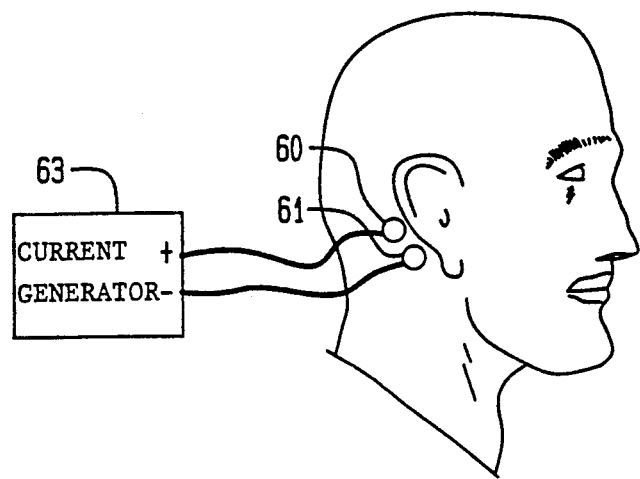
FIG. 6 shows an arrangement for introducing a controlled electrical stimulus to one ear of the subject.

FIG. 6 shows an arrangement for introducing a controlled electrical stimulus to one ear. A pair of small surface electrodes 60 and 61 are placed next to one another over the mastoid bone of the ear to be stimulated. A current generator 63 is connected by wires to the two electrodes. The generator passes low levels of current between the two electrodes.

Figure 7:
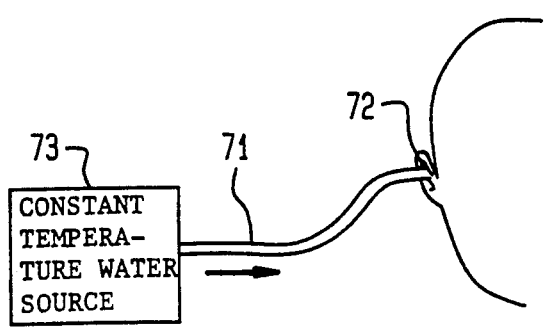
FIG. 7 shows an arrangement for introducing a controlled thermal stimulus to one ear of the subject.

FIG. 7 shows an arrangement for introducing a controlled thermal stimulus to one ear. A small tube 71 is placed in the external ear canal 72. The other end of the tube is connected to a source of constant temperature water 73. Water is then pumped through the tube to irrigate the ear.

FIG. 8 shows a preferred embodiment of a method according to the present invention. In this embodiment, a feedback loop 80–84 is created by positioning the subject on the support surface and within the visual enclosure with the body and head aligned in relation to the sway-reference axis of the support surface and visual enclosure, having the subject seek to maintain equilibrium 84, measuring the position of the vertical force center on the forceplate 80, calculating the displacement angle of the center of body mass from equilibrium 81, multiplying the displacement angle by a gain factor to compute the displacing angle of the support surface and visual enclosure 82, moving the support surface and/or visual enclosure by the computed displacing angle 83, stimulating the subject's vestibular system according to a desired protocol 85, storing the measures of vertical force center and body displacement angle on a continuous basis 86, pulse trigger averaging the force center and displacement angle measures with the vestibular stimuli 87, and then determining the extent to which the vestibular stimuli caused significant changes in the vertical force position and angular position measures 88. Alternatively, the body displacement angle can be measured directly 81' rather than calculated from the forceplate measurements.

FIGS. 9A–9C illustrate the sequence of events measured during an electrical test of the left superior and right inferior semicircular canal end organs conducted according to a preferred embodiment of the method shown in FIG. 8. Surface electrodes are placed over the mastoid bone of the left and then the right ear as shown in FIG. 6. The subject is positioned in relation to the support surface and visual enclosure sway-reference axis such that sensitive axes of the left superior and right inferior semicircular canal receptor end organs are aligned as shown in FIG. 3. The sway-reference gains for the visual enclosure and support surface are set and the visual enclosure and support surface are sway-referenced. Four measures of the subject's displacements from equilibrium, two ankle muscle EMG's 91 and 92, the antero-posterior position of the center of vertical force 93, and antero-posterior angular orientation of the center of body mass in relation to the ankles 94, are recorded by the computer on a continuous basis. Brief pulses of electrical current 90 are passed on a periodic basis between the two mastoid bone surface electrodes, while recording of the three measures of postural activity continues. Then, each of the three measures is ensemble averaged in segments 95 time-locked to the onset of the current pulses. Significant changes in any of the three ensemble averaged measures are identified on a continuous basis by statistical tests well known in the prior art.

In FIG. 9A, the support surface and visual enclosure are fixed (sway-reference gains of zero). The antero-posterior position of the vertical force center 93 and the angular displacement of the subject's center of body gravity with respect to the feet 94 move randomly as the subject stands erect. EMG traces from two ankle muscles 91 and 92 typically show little activity under this quiescent condition. After the subject has stood for a period of time, a series of brief current pulses 90 are introduced to the (normal) left ear. Ensemble averages of the four measures 96–99 show significant increases in the subject's displacement from equilibrium correlated with the current stimuli 90. This result indicates that the left superior canal end organ is normally sensitive to electrical stimulation. No further electrical testing of the left superior end organ is therefore required.

In FIG. 9B, the subject maintains the same position as described in FIG. 9A, and the rotational position of the support surface and visual enclosure are again fixed (i.e., sway-reference gains of zero). Now, after a period of quiescent standing, the current stimulus 90' is introduced to the (abnormal) right ear. With the surface fixed, no significant postural reactions are observable in the ensemble averages of any of the measurements 96', 97', 98', and 99'. This result indicates that the sensitivity of the right inferior canal end organ to external electrical stimulation is reduced and that this organ is therefore impaired.

In FIG. 9C, further testing of the right inferior canal is conducted to determine the extent of right inferior canal impairment. The subject's head remains turned to the left. The rotational orientation of the support surface and visual enclosure is now sway-referenced with gains of ¼. After a period of quiescent standing, the current stimulus 90" is again introduced to the (abnormal) right ear. With the surface sway-referenced at a gain of ¼, significant postural reactions are now observable in the ensemble average measurements 96", 97", 98", and 99". This result indicates that the sensitivity of the right superior canal end organ to external electrical stimulation is only partially impaired.

Table I summarizes how symmetrical and asymmetrical losses in vestibular function can be categorized according to the above described-vestibular function tests.

TABLE I

| | Vestibular Functional Loss Test | |
| | Postural Reaction to Stimulation | |
| Category | Ear A | Ear B |
| I. Bilateral Total Loss | No reactions at any sway-reference gain or head position | No reactions at any sway-reference gain or head position |
| II. Bilateral Partial Loss | Reactions at sway-referenced gains ≥ ¼ only in all head positions | Reactions at sway-referenced gains ≥ ¼ only in all head positions |
| III. Bilateral Selective Losses | Reactions in some head positions with sway-reference gains = 0, in others with gains ≥ ¼ only | Reactions in some head positions with sway-reference gains = 0, in others with gains ≥ ¼ only |
| IV. Unilateral Total Loss | No reactions at any sway-reference gain or head position | Reactions with fixed support and enclosure |
| V. Unilateral Partial Loss | Reactions at sway-referenced gains ≥ ¼ only in all head positions | Reactions with fixed support and enclosure |
| VI. Unilateral Selective Loss | Reactions in some head positions with sway-reference gains = 0, in others with gains ≥ ¼ only | Reactions with fixed support and enclosure |
| VII. Normal | Reactions with fixed support and enclosure | Reactions with fixed support and enclosure |

A subject is placed in category I (bilateral total loss) who shows no significant postural reactions to brief stimulation of either ear with all combinations of sway-reference gains and head positions in relation to the sway-reference axis. A subject who has reactions to brief stimulation of either ear in all head positions and with sway-referenced gains of ¼ or greater only is placed in category II (bilateral partial loss). A subject who reacts to brief stimulation of either ear at sway-reference gains of zero with the head in some positions in relation to the sway-reference axis and at sway-reference gains of ¼ or greater in other head positions is placed in category III (bilateral selective losses). A subject who does not react to stimulation of one ear under any and all combinations of sway-reference gain and head position in relation to the sway-reference axis, but who reacts to stimulation of the other ear with the support surface and visual enclosure fixed is placed in category IV (unilateral total loss). A subject is placed in category V (unilateral partial loss) who reacts to electrical stimulation of one ear with the support surface and visual enclosure fixed and in the other ear only with sway-referenced gains of ¼ or greater. A subject who reacts to brief stimulation of one ear at sway-reference gains of zero with the head in some positions in relation to the sway-reference axis and at sway-reference gains of ¼ or greater in other head positions, and who reacts to stimulation of the other ear with the support surface and visual enclosure fixed is placed in category VI (unilateral selective loss). All remaining subjects are placed in category N (normal).

In all examples of the vestibular functional loss test, electrical or thermal stimuli can be used. In all tests, including the perilymph fistula and vestibular functional loss tests, a support surface in which motions are actively controlled by a motor can be replaced with a support surface with viscoelastic compliant properties which moves passively in relation to the displacements of the subject from the maintained equilibrium position.

Figure 10:
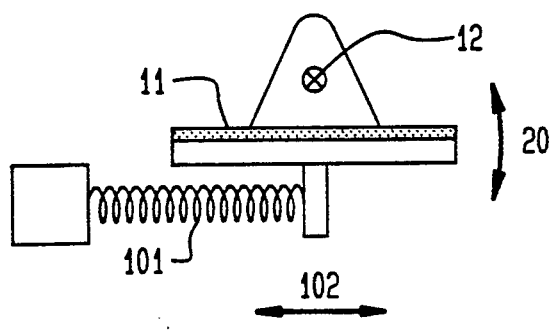
FIG. 10 shows an apparatus for providing a support surface which rotates in functional relation to a quantity related to the subject's displacement from equilibrium.

FIG. 10 shows much simpler means for providing a support surface which rotates in functional relation to a quantity related to the subject's displacement from equilibrium. The support surface 11 is made compliant about the axis of rotation 12 by restraining the rotational motion of the surface with a compliant element 101. The compliant element can have purely elastic properties, such as a linear spring, or it can have a combination of elastic and viscous properties, such as with a spring and fluid damper. Forces exerted by the subject against the support surface move the compliant element 102 and thereby rotate the support surface 11 in direction 20. It should also be appreciated that the visual enclosure can be connected to the compliant support surface, such that both of these components will move in functional relation to the subject.

In addition, variables for determining the subject's postural activity other than those described in the preferred embodiments can be used. For example, the front-to-back or side to side changes in orientation of the center of body mass can be measured with a potentiometer linked to the body with a belt and flexible coupling. Postural activity can also be measured by recording the electromyographic activity of one or more muscles providing postural support, using surface electrodes and high gain differential amplification.

What is claimed is:

1. A method for determining whether a subject placed in a position of equilibrium and maintaining this position while visual inputs are disrupted has an abnormal connection between the middle and inner ear space, such method comprising:
   A. placing the subject on support surface and having the subject assume a position in equilibrium;
   B. substantially surrounding the subject's field of view with a movable visual enclosure;
   C. measuring one or more quantities related to the subject's displacement from the equilibrium position;
   D. moving the visual enclosure in functional relation to one of the measured quantities;
   E. introducing to the external canal of one ear a controlled change in air pressure;
   F. determining whether the controlled change in pressure causes significant change in one or more of the measured quantities, the lack of such significant change indicating a normal connection between the middle and inner ear space.

2. A method for determining whether a subject placed in a position of equilibrium and maintaining this position while both support surface and visual inputs are disrupted has an abnormal connection between the middle and inner ear space, such method comprising:
   A. placing the subject on a movable support surface and having the subject assume a position in equilibrium;
   B. substantially surrounding the subject's field of view with a movable visual enclosure;
   C. measuring one or more quantities related to the subject's displacement from the equilibrium position;
   D. moving the support surface and visual enclosure in functional relation to one of the measured quantities;
   E. introducing to the external canal of one ear a controlled change in air pressure;
   F. determining whether the controlled change in pressure causes significant change in one or more of the measured quantities, the lack of such significant change indicating a normal connection between the middle and inner ear space.

3. An apparatus for determining the presence of a disorder in a human subject's vestibular system, the human subject having a field of view and musculoskeletal joints which may be bent to maintain the subject in an upright position, the apparatus comprising:
   a support surface, upon which the subject may assume an equilibrium position, from which the subject may have a displacement, the surface being rotatable about an axis that is substantially co-linear with musculoskeletal joints that the subject bends to maintain an upright position when the support surface is rotated;
   measurement means for measuring a quantity related to the subject's displacement from equilibrium;
   first movement means for rotating the support surface in functional relation to the measured quantity,
   stimulus means for applying an electrical stimulus to the subject's vestibular system;
   a visual enclosure, which substantially surrounds the subject's field of view and which is rotatable about an axis that is substantially co-linear with the axis of the rotation of the support surface;
   second movement means for moving the visual enclosure in functional relation to the measured quantity, and
   program means, in communication with the measuring means, the first and second movement means, and the stimulus means, for activating the first and second movement means, and the stimulus means in accordance with a diagnostic protocol.

4. An apparatus for determining the presence of a disorder in a human subject's vestibular system, the human subject having a field of view and musculoskeletal joints which may be bent to maintain the subject in an upright position, the apparatus comprising:
   a support surface, upon which the subject may assume an equilibrium position, form which the subject may have a displacement, the surface being rotatable about an axis that is substantially co-linear with musculoskeletal joints that the subject bends to maintain an upright position when the support surface is rotated;
   measurement means for measuring a quantity related to the subject's displacement from equilibrium;
   first movement means for rotating the support surface in functional relation to the measured quantity;
   stimulus means for applying a thermal stimulus to the subject's vestibular system;
   a visual enclosure, which substantially surrounds the subject's field of view and which is rotatable about an axis that is substantially co-linear with the axis of the rotation of the support surface;
   second movement means for moving the visual enclosure in functional relation to the measured quantity; and
   program means, in communication with the measuring means, the first and second movement means, and the stimulus means, for activating the first and second movement means, and the stimulus means in accordance with a diagnostic protocol.

5. An apparatus for determining the presence of a disorder in a human subject's vestibular system, the human subject having a field of view and musculoskeletal joints which may be bent to maintain the subject in an upright position, the apparatus comprising:
- a support surface, upon which the subject may assume an equilibrium position, from which the subject may have a displacement, the surface being rotatable about an axis that is substantially co-linear with musculoskeletal joints that the subject bends to maintain an upright position when the support surface is rotated;
- measurement means for measuring a quantity related to the subject's displacement from equilibrium;
- first movement means for rotating the support surface in functional relation to the measured quantity;
- stimulus means for applying a pressure stimulus to the subject's vestibular system;
- a visual enclosure, which substantially surrounds the subject's field of view and which is rotatable about an axis that is substantially co-linear with the axis of the rotation of the support surface;
- second movement means for moving the visual enclosure in functional relation to the measured quantity; and
- program means, in communication with the measuring means, the first and second movement means, and the stimulus means, for activating the first and second movement means, and the stimulus means in accordance with a diagnostic protocol.

6. A method for increasing the sensitivity of a human subject's vestibular system to a controlled external stimuli, the subject having a field of view and musculoskeletal joints which may be bent to maintain the subject in an upright position, the method comprising:
- A. placing the subject upon a support surface, which is rotatable about an axis that is substantially co-linear with the musculoskeletal joints that the subject bends to maintain an upright position when the support surface is rotated;
- B. having the subject to assume a position of equilibrium on the support surface, from which the subject may have a displacement;
- C. measuring a quantity related to the subject's displacement from equilibrium;
- D. rotating the support surface in functional relation to the measured quantity,
- E. surrounding substantially the subject's field of view with a visual enclosure, which is rotatable about an axis that is substantially co-linear with the axis of rotation of the support surface; and
- F. moving the visual enclosure in functional relation to the measured quantity.

7. A method according to claim 6, wherein the subject has ankle joints, step A includes placing the subject in an upright standing position on the support surface, and the support surface is rotatable about an axis co-linear with the subject's ankle joints.

8. A method according to claim 6, wherein the subject has hip joints, step A includes placing the subject in a sitting position on the support surface, and the support surface is rotatable about an axis co-linear with the subject's hip joints.

9. A method for increasing the sensitivity of a human subject's vestibular system to a controlled external stimuli, the subject having a field of view and ankle joints, the method comprising:
- A. placing the subject in an upright standing position on a support surface, which is rotatable about a sway-reference axis, such that the subject's ankle joints define an axis substantially perpendicular to the sway-reference axis, and such that the subject may have a lateral displacement;
- B. having the subject to assume a position of equilibrium on the support surface;
- C. measuring a quantity related to the subject's lateral displacement form equilibrium;
- D. rotating the support surface in functional relation to the measured quantity;
- E. surrounding substantially the subject's field of view with a visual enclosure, which is rotatable about the sway-reference axis; and
- F. moving the visual enclosure in functional relation to the measured quantity.

10. A method for determining the responsiveness of an inner ear vestibular end organ of a human subject to an external stimulus, the vestibular end organ having a sensitive axis, such method comprising:
- A. placing the subject on a support surface rotatable about a sway-reference axis;
- B. positioning the subject in relation to the sway-reference axis such that the sensitive axis of the vestibular end organ is aligned with the sway-reference axis;
- C. having the subject assume a position in equilibrium, from which the subject may have a displacement;
- D. measuring a quantity related to the subject's displacement from the equilibrium position;
- E. causing the support surface to undergo changes in angular orientation in functional relation to the subject's displacement;
- F. introducing to the subject's vestibular end organ a controlled external vestibular stimulus; and
- G. determining whether or not the external stimulus produces significant correlated changes in the measured quantity, a lack of significant correlated changes indicating that the vestibular end organ is non-responsive.

11. A method according to claim 10, wherein the subject has eyes, which are closed during steps E-F.

12. A method according to claim 10, wherein the subject has a field of view, step A further includes substantially surrounding the subject's field of view with a movable visual enclosure, and step E further includes causing the visual enclosure to undergo changes in angular orientation in functional relation to the subject's displacement.

13. A method according to claim 10, wherein step E further includes making the support surface compliant about the sway-reference axis.

14. A method according to claim 13, wherein the subject has eyes, which are closed during steps E-F.

15. A method according to claim 13, wherein the subject has a field of view and step A further includes substantially surrounding the subject's field of view with a movable visual enclosure, and wherein step E further includes attaching the visual enclosure to the support surface such that the two surfaces rotate together about the same sway-reference axis.

16. A method for determining the extent of functional loss in a human subject's vestibular system, such method comprising:

A. having the subject assume a position in equilibrium, from which the subject may have a displacement;
B. placing the subject on a support surface which is fixed in a horizontal position;
C. measuring a quantity related to the subject's displacement from the equilibrium position;
D. while the subject is on the support surface which is fixed, introducing to the subject's vestibular system a controlled external stimulus;
E. determining whether or not the external stimulus introduced in step D causes significant correlated changes in the measured quantity;
F. placing the subject on a support surface which is rotatable about a sway-reference axis, and sway-referencing the rotatable support surface by causing the support surface to undergo changes in functional relation to the subject's displacement;
G. while subject is on the sway-referenced support surface, introducing to the subject's vestibular system a controlled external stimulus;
H. determining whether or not the external stimulus introduced in step G produces significant correlated changes in the measured quantity; and
I. determining based on the determinations of steps E and H the extent of functional loss.

17. A method according to claim 16, wherein the subject has a field of view, and step F further includes substantially surrounding the subject's field of view with a visual enclosure rotatable about the sway-reference axis, and causing the visual enclosure to undergo changes in angular orientation in functional relation to the subject's displacement.

18. A method for determining whether a human subject's middle and inner ear space has an abnormal connection that selectively affects a specific vestibular end organ, the subject having a head and an external ear canal, and the vestibular end organ having a sensitive axis, such method comprising:
    A. placing the subject on a support surface rotatable about a sway-reference axis;
    B. positioning the subject's head such that the sensitive axis of the vestibular end organ is aligned with the sway-reference axis;
    C. having the subject assume a position in equilibrium, from which the subject may have a displacement;
    D. measuring a quantity related to the subject's displacement from the equilibrium position;
    E. causing the support surface to undergo changes in angular orientation in functional relation to the subject's displacement;
    F. introducing to the external ear canal a controlled change in air pressure; and
    G. determining whether the controlled change in air pressure produces a significant change in the measured quantity, lack of such significant change indicating an abnormal connection between the middle and inner ear space that selectively affects the vestibular end organ.

19. A method according to claim 18, wherein the subject has eyes, which are closed during steps C-F.

20. A method according to claim 18, wherein the subject has a field of view, and step A further includes substantially surrounding the subject's field of view with a visual enclosure rotatable about the sway-reference axis, and step E further includes causing the visual enclosure to undergo changes in angular orientation in functional relation to the measured quantity.

21. A method according to claim 18, wherein step E further includes making the support surface compliant about the sway-reference axis.

22. A method according to claim 21, wherein the subject has a field of view, and step A further includes substantially surrounding the subject's field of view with a visual enclosure rotatable about the sway-reference axis, and step E further includes attaching the visual enclosure to the support surface such that the two surfaces rotate together about the sway-reference axis.

23. A method for determining whether a human subject has functional losses selectively affecting vestibular end organs of an ear of the subject, the subject having a head, and the vestibular end organs having sensitive axes, such method comprising:
    A. placing the subject on a support surface rotatable about a sway-reference axis;
    B. positioning the subject's head such that the sensitive axis of one vestibular end organ of the ear is aligned with the sway-reference axis;
    C. having the subject assume a position in equilibrium, from which the subject may have a displacement;
    D. measuring a quantity related to the subject's displacement from the equilibrium position;
    E. causing the support surface to undergo changes in angular orientation in functional relation to the subject's displacement;
    F. introducing a controlled external stimulus to one of the subject's ear;
    G. determining whether the controlled stimulus produces significant correlated reactions in the measured quantity;
    H. repeating steps C through G with the subject's head positioned such that the sensitive axes of each vestibular end organ of the ear is in turn aligned with the sway-reference axis; and
    I. comparing the correlated reactions so produced, the lack of significant correlated reactions in one head position and the presence of significant correlated reaction in another head position indicating a selective functional loss affecting the vestibular end organs.

24. A method according to claim 23, wherein the subject has a field of view, and step B further includes substantially surrounding the subject's field of view with a visual enclosure rotatable about the sway-reference axis, and step D further includes causing the visual enclosure to undergo changes in angular orientation in functional relation to the subject's displacement.

25. A method according to claim 23, wherein the subject has eyes, which are closed during steps C-G.

26. A method according to claim 23, wherein the subject has a second ear, step H further includes repeating steps C through G with the subject's second ear exposed to the controlled external vestibular stimulus, and step I further includes comparing the correlated reactions produced by introducing the stimulus to the ears.

27. A method according to claim 23, wherein step E further includes making the support surface compliant about the sway-reference axis.

28. A method for determining the presence of a disorder in a human subject's vestibular system, the method comprising:

A. placing the subject on a support surface rotatable about a sway-reference axis, the subject having an angular orientation about the sway-reference axis;
B. fixing the support surface in a horizontal position;
C. having the subject assume a position in equilibrium, from which the subject may have a displacement;
D. measuring a quantity related to the subject's displacement from equilibrium;
E. introducing a stimulus to the subject's vestibular system;
F. determining whether significant increases have occurred in the measured quantity with the introduction of the stimulus;
G. sway-referencing the support surface by:
   (1) measuring changes in the angular orientation of the subject; and
   (2) causing the support surface to incline in proportion to the measured change in the subject's angular orientation;
H. while the support surface is sway-referenced, repeating steps C through F; and
I. determining, based on the presence or absence of significant increases in the measured quantity, whether the subject has a vestibular disorder.

29. A method according to claim 28, wherein the subject has a field of view, step A further includes substantially surrounding the subject's field of view with a movable visual enclosure, step G further includes sway-referencing the visual enclosure by causing the visual enclosure to rotate in proportion to the measured change in the subject's angular orientation, and step H is performed while the visual enclosure is also sway-referenced.

30. A method according to claim 28, wherein the step G the support surface is caused to incline a fraction of the measured change in the subject's angular orientation, such that changes between the subject's orientation angle and the inclination of the support surface are reduced.

31. A method according to claim 30, wherein the subject has a field of view, step A further includes substantially surrounding the subject's field of view with a movable visual enclosure, step G further includes sway-referencing the visual enclosure by causing the visual enclosure to rotate a fraction of the measured change in the subject's angular orientation, and step H is performed while the visual enclosure is also sway-referenced.

* * * * *

UNITED STATES PATENT AND TRADEMARK OFFICE
CERTIFICATE OF CORRECTION

PATENT NO. : 5,303,715
DATED : April 19, 1994
INVENTOR(S) : Lewis M. Nashner, F. Owen Black, David J. Lilly It is certified that error appears in the above-indentified patent and that said Letters Patent is hereby corrected as shown below:

| | |
|---|---|
| column 15, line 36 | "on support surface" should be --on a support surface-- |
| column 16, line 23 | "measured quantity," should be --measured quantity;-- |
| column 16, line 31 | "measured quantity," should be --measured quantity;-- |
| column 16, line 44 | "form" should be --from-- |
| column 17, line 47 | "measured quantity," should be --measured quantity;-- |
| column 18, line 10 | "form" should be --from-- |
| column 22, line 10 | "the" should be --in-- |

Signed and Sealed this

Sixth Day of December, 1994

Attest:

BRUCE LEHMAN

*Attesting Officer*     *Commissioner of Patents and Trademarks*